(12) United States Patent
McVicker

(10) Patent No.: US 6,267,947 B1
(45) Date of Patent: Jul. 31, 2001

(54) WATER RESISTANT PESTICIDE COMPOSITION

(75) Inventor: Nola Janene McVicker, Carterville, IL (US)

(73) Assignee: Sun Glitz Corporation, Energy, IL (US)

( * ) Notice: Subject to any disclaimer, the term of this patent is extended or adjusted under 35 U.S.C. 154(b) by 0 days.

(21) Appl. No.: 08/173,376

(22) Filed: Dec. 23, 1993

(51) Int. Cl.[7] ................................ A01N 25/06
(52) U.S. Cl. ..................... 424/45; 424/405; 424/407; 424/DIG. 10; 514/718
(58) Field of Search ................... 424/405, 407, 424/45, 59, DIG. 10; 514/781

(56) References Cited

U.S. PATENT DOCUMENTS

| | | | |
|---|---|---|---|
| 3,060,084 | 10/1962 | Littler | 167/42 |
| 3,178,350 | 4/1965 | Lund | 167/78 |
| 3,576,760 | 4/1971 | Gould et al. | 252/403 |
| 3,966,902 * | 6/1976 | Chromecek | 424/59 |
| 3,975,350 | 8/1976 | Hudgin et al. | 260/30.4 |
| 4,457,910 * | 7/1984 | Van Cleave | 424/59 |
| 4,520,015 * | 5/1985 | Pesche | 424/153 |
| 4,808,615 | 2/1989 | Ott et al. | 514/89 |
| 4,981,689 | 1/1991 | Shikinami et al. | 424/409 |
| 5,221,535 | 6/1993 | Domb | 424/450 |
| 5,221,698 * | 6/1993 | Amidon et al. | 523/122 |
| 5,227,163 | 7/1993 | Eine et al. | 424/195.1 |

OTHER PUBLICATIONS

"Personal Care Polymers", RESYN® 28–2930 product brochure, National Starch and Chemical Company, Bridgewater, New Jersey; ©1994 National Starch and Chemical Company.

* cited by examiner

*Primary Examiner*—Neil S Levy
(74) *Attorney, Agent, or Firm*—Barnes & Thornburg

(57) ABSTRACT

An improved long acting pesticide formulation is described. A water swellable polycarboxylated polymer is dissolved in a solution/suspension of a pesticide formulation in a substantially non-aqueous liquid carrier. The composition, upon topical application, dries to a surface adherent polymer matrix film that swells responsive to contact with water/ambient humidity to effect prolonged pesticidal efficacy.

2 Claims, No Drawings

WATER RESISTANT PESTICIDE COMPOSITION

BACKGROUND AND SUMMARY OF THE INVENTION

This invention relates to novel pesticide compositions and methods for their use in topical veterinary topical applications. More particularly, this invention is directed to water/perspiration resistant pesticide compositions comprising a solution of a water swellable polycarboxylated polymer and a pesticide in a substantially nonaqueous liquid carrier.

There are many species of biting insects, including mosquitoes, ticks, mites, and horse flies, which prey upon vertebrate species. These insect species not only inflict discomfort by their bites, but they also can transmit disease. The sharp pain associated with insect bites can indirectly result in other injury when, for example, the animal reacts with sudden unexpected reflexive movements. Since the timing of an insect's bite is unpredictable, a docile animal may react in a sudden violent manner. This is especially a problem for equestrians. Horses are frequently bitten by horseflies causing them to bolt unexpectedly, throwing their rider. For these reasons it is desirable to protect vertebrate species, and in particular domesticated animals, from being bitten by insects.

One means of protecting animals from biting insects is to treat the animal with an insecticide or insect repellent. Pesticides suitable for such uses are well known to those familiar with the art, and as used herein the term "pesticide" embraces insecticides, herbicides, fungicides, nematocides, miticides, bactericides, pest repellents, and combinations thereof. Typically, pesticide formulations for veterinary use are applied as a spray, lotion, cream or powder to the animal. Although currently available pesticidal formulations are effective to prevent insects from biting animals, their efficacy is diminished due to their water solubility; as the pesticide treated animal surface (typically hair or skin) comes into contact with water, the pesticide is washed from the treated surface. Topically applied pesticide formulations are often prematurely washed from the treated surface by rain, or as an animal becomes active, the animal's own perspiration. Removal of the applied pesticide renders the animal susceptible to insect attack.

It would thus be desirable to provide a topical pesticide composition for veterinary use that is easy to apply and capable of sustained retention on the treated surface in the presence of water. It is also desirable that such composition be readily washable from the surface when pesticidal functionality is no longer necessary.

The present invention provides a pesticide composition suitable for topical application to an animal or other surface exposed to humid or wet conditions. The composition comprises a solution of a water swellable hydrophilic polymer and a pesticide in a substantially nonaqueous liquid medium. Advantageously, the hydrophilic polymer functions to entrap the pesticide within the polymer matrix and also exhibits good affinity to the surface. The surface applied pesticide formulation is resistant to being washed from the surface by the perspiration of the animal and thus provides prolonged protection from insect bites even while the animal is active. Indeed, ambient humidity and moisture from other sources co-act with the applied pesticide/polymer matrix to swell the matrix and facilitate pesticide release from the matrix.

The present pesticide composition is formulated for rapid evaporation at ambient temperatures. When applied to animal coats, it evaporates to provide a surface adherent layer of the pesticide entrapping polymer matrix. As the animal becomes active, the polymer matrix becomes hydrated, both from animal perspiration and/or from ambient moisture, swells and thereby allows the pesticide to diffuse from the matrix. Thus, the polymer matrix formed during drying of the present composition functions to provide sustained insect protection to the animal not only by increasing the adherence of the pesticide formulation to the animal (more specifically to its skin or surface hair), but also by functioning to gradually release effective quantities of pesticide formulation.

In another embodiment of this invention there is provided the method of prolonging the pesticidal efficacy of a topical pesticide formulation comprising the pesticide in a substantially non-aqueous liquid carrier. The method comprises the step of dissolving about 0.25% to about 10% by volume of a water swellable polycarboxylated polymer in said pesticide formulation. The formulation can be applied topically and after allowing time for the liquid carrier to evaporate, provide prolonged topical pesticidal activity to prevent or reduce insect bites.

Additional objects, features, and advantages of the invention will become apparent to those skilled in the art upon consideration of the following detailed description of preferred embodiments exemplifying the best mode of carrying out the invention as presently perceived.

DETAILED DESCRIPTION OF THE INVENTION

In accordance with this invention there is provided a topical, perspiration/water resistant pesticide composition, particularly adapted for topical veterinary applications. Pesticide formulations, including particularly insect repellents and insecticides are well known in the art. Known pesticides suitable for use in the present composition are disclosed in U.S. Pat. No. 3,576,760 issued Apr. 27, 1971 and U.S. Pat. No. 3,060,084, issued Oct. 23, 1962, specifically incorporated herein by reference. The most widely used insect repellant is N,N-diethyl-m-toluamide, however, other compounds recognized for their insect repellant properties include Ethohexadiol, dimethyl phthalate, dimethyl ethyl hexanediol carbate and butopyronoxyl [butyldimethyl dihydro-gamma-pyrone carboxylate].

In one preferred embodiment of this invention, the pesticide formulation comprises a nonaqueous solution of a water swellable polycarboxylated polymer and permethrin and pyrethrins. Pyrethrins are the active insecticidal constituents of pyrethrum flowers (Chrysanthemums). Although Pyrethrins are an effective insecticide, their use is limited because they will oxidize and become inactive in air. Permethrin [3-(phenoxyphenyl) methyl (±)-cis,trans-3(2,2-dichloroethenyl)-2,2-dimethyl cyclopropanecarboxylate] is a more stable compound that provides long lasting pesticidal activity. These two pesticides are often combined with piperonyl butoxide, which blocks detoxification of the pyrethrins by the insect, and/or an insect repellant such as N-octyl bicycloheptene dicarboximide.

When formulated as a nonaqueous or substantially non-aqueous solution/suspension, pesticides can be combined with a water swellable polycarboxylated polymer to provide a water-resistant formulation in accordance with this invention particularly adapted for topical veterinary use. Such a formulation represents an improvement over prior art pesticide formulations in that the polymer-pesticide combination provides sustained protection from insect bites to a perspiring animal. The pesticidal efficacy of the pesticide formulation is prolonged due to the enhanced retention of the polymer (and the entrapped pesticide ingredients) on the animal's hair and skin, and as well the prolonged water-mediated release of the pesticide(s) from the applied polymer matrix. Advantageously, the present composition remain bound to an animal's hair and skin upon exposure to water, but can be removed by a detergent solution.

Hydrophilic polymers suitable for use in accordance with this invention are water swellable polymers that are soluble in the substantially nonaqueous solvent used as the fluid carrier for the formulation — at least soluble to the extent necessary for dissolution of functional amounts of the polymer in the present compositions. Preferred polymers for use in this invention are water swellable polycarboxylated polymers, including homopolymers or copolymers of acrylic acid or methacrylic acid.

One preferred group of polymers exhibiting the described functionality in accordance with this invention are those manufactured by the BF Goodrich Chemical Company under the trademark Carbopol®. Carbopol resins are acrylic acid polymers that have a strong affinity for water, and thus can be used to form surface adherent, water swellable matrices or films from substantially non-aqueous solutions. Preferably the polycarboxylated polymers used to form the present compositions are not crosslinked and have molecular weights ranging from $8 \times 10^5$ to about $4 \times 10^6$, but most preferably less than about $2 \times 10^6$.

The concentration of polymer component of the present pesticide compositions determines the viscosity of the pesticide composition and its water-resistance characteristic. The polymer must be used at a concentration sufficient to provide a surface adherent film which entraps the pesticide and works to resist removal of the pesticide by water following evaporation of the carrier liquid. Generally the water swellable polycarboxylated polymer is used at a level of abut 0.15 to about 10%, more preferably about 0.25 to about 5% by volume of dry polymer to pesticide carrier volume. The upper limit of polymer concentration is defined by the requirement that the pesticide composition must be suitable for topical application. High concentrations of polymer will have the undesirable effect of making the composition too viscous resulting in a sticky, tacky or gel-like composition that is difficult to apply to the surface of an animal.

The total pesticide concentration in the present compositions range from bout 1% to about 40%, more typically from about 2 to about 20%. The amount of pesticide is not critical except to the extent that it be used in pesticidally effective amounts; generally it is desirable to use the lowest effective concentration to minimize possibility of toxic side effects.

The present compositions comprise a solution of a water swellable hydrophilic polymer and a pesticide in a substantially nonaqueous liquid carrier. For the purpose of describing this invention, the term "substantially nonaqueous" means less than 5% water, more preferably less than 1% water, most preferably substantially anhydrous. The choice of the nonaqueous liquid carrier is functionally important to the efficacy of the present compositions. Firstly, it is desirable that the pesticidal compositions dry rapidly upon application to the surface of the animal. Thus a preferred liquid carrier is one that has good volatility and has reasonably short drying times. Secondly, because the polycarboxylated polymer ingredient has a high affinity for water, the liquid carrier is most preferably a substantially nonaqueous solvent. The presence of substantial amounts of water in the solvent can impede dissolution of the polymer and markedly decrease the adherence of the dried pesticide/polymer composition to the surface of the animal.

Preferred solvents are $C_1$–$C_4$ alcohols, $C_1$–$C_4$ alkane diols, and $C_1$–$C_4$ ketones and $C_1$–$C_6$ ether alcohols. Preferably these solvents contain less than 5% water, and more preferably less than 1%; most preferably the solvent is substantially anhydrous. Most preferred solvents are $C_1$–$C_4$ alcohols.

In one preferred embodiment, preparation of the pesticide composition entails dissolving the water swellable polycarboxylated polymer in a pesticide solution by blending the composition in a high speed blender. The composition is first blended at a low speed to initially disperse the polymer and then at a high speed to completely dissolve the polymer and homogenize the composition.

Pesticide compositions in accordance with this invention were tested for their surface affinity (water resistance) and time of drying. The testing procedures consist of coating a glass slide by dipping it in a test solution or placing a drop of a polymer/pesticide test formulation on a glass slide, tilting the glass slide to create a uniform layer of pesticide composition on the slide, and air drying the composition. Observations were made to determine the drying time. After the slides are air dried for 30 minutes, they are dipped in tepid tap water four or five times to attempt to wash the composition from the slide surface. The slide is then examined to determine if the composition remains bound to the slide. Because the dried pesticide compositions are typically transparent on the slide, determination of the composition's retention on the glass slide is accomplished by cleansing a portion of the slide with detergent. In general, a cotton swab soaked in a detergent solution is rubbed through the center of the slide to remove a portion of the composition coating, if any remains after the water rinsing steps. Then after rinsing the slide in water, diffraction of light allows visualization of any remaining coating of pesticide formulation.

The present pesticide compositions can be applied directly to an animal through the use of a brush or a sponge. However, preferred application is with the use of an aerosol or mechanical sprayer. For optimum use of the present composition as a topical veterinary pesticide, the animal's surface (coat) should be dry at the time of application of the pesticide composition. Further the applied composition should be allowed to dry before exposing the animal to wet conditions or exercising the animal.

EXAMPLE 1

Five cc of Carbopol 1342 (a polyacrylic acid having a molecular weight of about $1.3 \times 10^6$) is blended under high shear mixing conditions with 235 cc of a commercially available pesticide formulation comprising: 0.2% Permethrin, 0.2% pyrethrins, 0.5% piperonyl butoxide technical, 2% N-octyl bicycloheptene dicarboximide, 1% Di-N-propyl isocinchomeronate, 5% butoxypolypropylene glycol, 0.75% PABA, and 1.25% lanolin dissolved in isopropyl alcohol. The formulation exhibits excellent surfactant affinity and good pesticidal repellant characteristics. It can be sprayed on a horse before exercise/riding and provide prolonged insect resistance even with heavy perspiration associated with hard exercise.

What is claimed is:

1. A method for preventing insects from biting a vertebrate species, said method consisting essentially of the steps of topically applying a pesticide composition to a surface of said vertebrate species, said composition consisting essentially of about 0.25 percent to about 10 percent by volume of a water swellable polycarboxylated homopolymer or copolymer and an effective amount of a pesticide in a volatile non-aqueous solvent, drying the applied pesticide composition to form a surface adherent non-aqueous film of the polymer and pesticide on the vertebrate surface, and thereafter contacting the dried film with water to swell the film and promote release of the pesticide from the surface adherent film.

2. The method of claim 1, wherein the application step comprises spraying the pesticide composition onto a vertebrate species.

* * * * *